United States Patent [19]

Hällgren et al.

[11] 4,153,417

[45] May 8, 1979

[54] METHOD OF INDICATING RHEUMATOID FACTORS

[75] Inventors: Henning R. Hällgren, Upplands-Bälinge; Leif E. Wide, Uppsala, both of Sweden

[73] Assignee: Pharmacia Diagnostics AB, Uppsala, Sweden

[21] Appl. No.: 818,646

[22] Filed: Jul. 25, 1977

[30] Foreign Application Priority Data

Sep. 8, 1976 [SE] Sweden .............................. 7609906

[51] Int. Cl.² ............................................. G01N 33/16
[52] U.S. Cl. ................................. 23/230 B; 23/230.6; 195/103.5 A; 424/1; 424/8; 424/12
[58] Field of Search ............... 23/230 B, 230.6; 424/8, 424/12, 1; 195/103.5 A

[56] References Cited

U.S. PATENT DOCUMENTS

| 3,594,466 | 7/1971 | Lille | 424/12 |
|---|---|---|---|
| 3,658,982 | 4/1972 | Reiss | 424/12 |
| 3,689,632 | 9/1972 | Mizushima | 424/12 |
| 4,062,935 | 12/1977 | Masson | 424/12 |

OTHER PUBLICATIONS

Chemical Abstracts, 71:58955x (1969).
Chemical Abstracts, 74:2303c (1971).

*Primary Examiner*—Sidney Marantz
*Attorney, Agent, or Firm*—Fred C. Philpitt

[57] ABSTRACT

A method of indicating rheumatoid factors belonging to at least one of the immunoglobulin classes IgM, IgG and IgA in an aqueous sample is disclosed. According to this method any complement factor C1q present in the sample is pacified in a manner known per se, whereafter the sample is reacted with soluble, aggregated immunoglobulin labelled with one or more analytically indictable atoms or groups to form aggregates between rheumatoid factors and the aggregated, labelled immunoglobulin, said aggregate being precipitated out, whereafter the precipitate is separated and the analytically indicatable atoms or groups are indicated in the precipitation phase and/or in the solution.

2 Claims, No Drawings

METHOD OF INDICATING RHEUMATOID FACTORS

The present invention relates to a method of indicating rheumatoid factors belonging at least to one of the immunoglobulin classes IgM, IgG and IgA in an aqueous sample.

Anti-immunoglobulins are also designated rheumatoid factors and may belong to the immunoglobulin classes IgM, IgG, IgA or, possibly, also to other immunoglobulin classes. In turn, rheumatoid factors may be directed against immunoglobulins belonging to the classes IgG or IgM or possibly against other immunoglobulin classes, which immunoglobulins have been changed in structure due to immune complex formation or aggregation.

Previously suggested test methods for indicating rheumatoid factors are based on the agglutination of, for example, blood corpuscles or latex particles coated with IgG. These methods indicate primarily rheumatoid factors of the IgM-type directed against changed IgG. Samples taken from most patients suffering from rheumatoid arthritis show a positive result in such a test, although samples from 20–30% show a negative result.

In accordance with the present invention there is now provided a method of indicating rheumatoid factors in an aqueous sample, said method indicating all rheumatoid factors in the sample in a manner which is more complete than was possible with the previously known methods, i.e. also rheumatoid factors which do not belong to the immunoglobulin class IgM and which could not be previously indicated to the desired extent in the presence or the absence of such factors belonging to the IgM class.

The method according to the invention is characterised by the fact that any complement factor C1q present in the sample is pacified in a manner known per se, whereafter the sample is reacted with soluble, aggregated immunoglobulin labelled with one or more analytically indicatable atoms or groups to form aggregates between rheumatoid factors and the aggregated, labelled immunoglobulin, which aggregates are precipitated out, whereafter the precipitate is separated and the analytically indicatable atoms or groups are indicated in the precipitation phase and/or in the solution.

The complement factor C1q in the sample may, for example, be pacified by heating the sample or by adding thereto diaminobutane or deoxyribonuecleic acid in a manner known per se.

Soluble, aggregated immunoglobulin can be prepared, for example, by heating a solution of an immunoglobulin or by chemical treatment with bis-diazotized benzidine or di-(4-aminophenyl)-sulphone (cf. Handbook of Experimental Immunology, Second Ed., Edited by D.M. Weir, Blackwell Scientific Publications, Oxford, 1976, page 10.75) and subsequently separating soluble, aggregated immunoglobulin from monomeric immunoglobulin and from any minor quantities of insoluble aggregates formed, by gel filtration. Preferably, the immunoglobulin used in this context is belonging to the IgG-class. The immunoglobulin is not aggregated more than that the major portion of the aggregated immunoglobulin is still soluble in the aqueous sample.

For labelling the aggregated immunoglobulin, there can be use any analytically indicatable atom or group known with regard to the labelling of immunoglobulins. Thus, labelling of aggregated immunoglobulins with a radioactive isotope can be effected in a conventional manner, there being selected for this purpose a suitable isotope, such as $^{125}I$ (see for example the method according to Hunter and Greenwood, Nature, volume 194, 1962, page 495). Similarly, labelling can be effected with a fluorescent group in a conventional manner, for example with the aid of a fluorescein derivative, such as fluorescein isothiocyanate. Labelling may also be effected with an enzymatically active group or with groups containing free radicals for indicating purposes.

In order to obtain a more complete precipitation of the obtained aggregates between rheumatoid factors and the aggregated labelled immunoglobulin, methods known per se in connection with the precipitation of macromolecules can be made use of. For instance, there may be added a water-soluble, uncharged polymer of the type which can be used to facilitate precipitation of macromolecules (e.g. in connection with immunological reactions for facilitating the precipitation of antibody-antigen complexes) by reducing the liquid volume in the solution accessible to the macromolecules by so-called steric exclusion, thereby to reduce the solubility of the macromolecules (see for example Hellsing, Acta Chem. Scand. 20 (1966) page 1251). Examples of such polymers include water-soluble polyethylene glycols, polysaccharides and (uncharged) polysaccharide derivatives, e.g. dextran and water-soluble cellulose derivatives. Although the polymer is preferably added before the reaction takes place it may also be added during or after the reaction process. The amount of polymer added is selected in all cases in a manner such that the polymer concentration lies immediately beneath that at which precipitation of any of the individual components taking part in the reaction (i.e. primarily aggregated, labelled immunoglobulin) is obtained. Suitable concentrations can be readily established by simple tests.

The invention will now be described with reference to a specific example.

EXAMPLE

A. Preparation of aggregated human-IgG (agg IgG)

Human-IgG (fraction II from Cohn-fractionation) from combined human sera was obtained from Kabi AB, Sweden and was heated in the form of a 2% IgG-solution for 20 minutes at 60° C. The thus obtained aggregated IgG (agg IgG) was separated from monomeric IgG by gel-filtration on a 90×1.5 cm column containing particles of dextran cross-linked with epichlorohydrin (Sephadex$^{(R)}$ G-200 from Pharmacia Fine Chemicals AB, Sweden) and equilibrated with 0.1 M tris(hydroxymethyl)-aminomethane-HCl-buffer containing 0.5 M NaCl having a pH 7.4. Concentrations of agg IgG were determined spectrophotometrically at 280 nm.

B. Preparation of labelled agg IgG

To 20 μl of a solution containing 40 μg agg IgG obtained according to A above were added 500 μCi Na $^{125}I$ and 10 μl of 0.5 M sodium phosphate buffer having a pH 7.4 and 10 μg of chloramine T in 10 μl water. After 50 seconds, 24 μg of sodium methabisulphite were added. The reaction mixture was separated on Sephadex$^{(R)}$ G-200 (i.e. gel particles consisting of dextran cross-linked with epichlorohydrin), the first fraction with the void volume being recovered. The eluted, labelled agg IgG was centrifuged at 3,500 g for 5 minutes to remove spontaneously precipitatable IgG. The labelled protein was diluted to approximately 40 μg/l (40,000 cpm in 0.1 ml) with a buffer solution prepared from 500 ml of 0.1 M sodium phosphate buffer having a pH 7.5, 500 ml of 0.15 M NaCl, 10 ml of 5% (w/v) NaN$_3$ and 5 ml of Tween$^{(R)}$ 20 (i.e. polyoxyethylene (20) sorbitan monolaurate).

C. Determination of rheumatoid factor-activity

Blood samples were taken aseptically from patients and permitted to clot at room temperature, whereafter they were centrifuged at 3,000 g and serum recovered. The serum was heat treated for 30 minutes at a temperature of 56° C.

The serum was then diluted to 1:40 with a solution having the following composition: 500 ml of 0.1 M sodium phosphate buffer pH 7.5, 500 ml of 0.15 M NaCl, 10 ml of 5% NaN$_3$, 5 ml of Tween$^{(R)}$ 20 and 2 g of polyethylene glycol (molecular weight 6,000). 400 μl of said serum dilution and 100 μl of I$^{125}$ labelled agg IgG (40,000 cpm) (obtained according to B) were charged to plastic tubes. The tubes were plugged and the contents incubated under constant rotation for 16 hours at +4° C. Thereafter the contents of the tubes were centrifuged at 3,500 g for 3 minutes. The plastic plugs were removed and 2 ml of a 0.9 M NaCl solution containing 0.5% Tween$^{(R)}$ 20 were added to each tube. The contents of the tubes were centrifuged at 3,500 g for 3 minutes. The supernatant was removed by suction. This washing procedure was repeated three times. The tubes were then plugged and placed in an automatic gamma counter.

High measurement values were obtained with samples taken from patients suffering from rheumatoid arthritis. Compared with conventional measuring techniques, better agreement was obtained between the measuring results and clinical diagnosis when using the present method.

28 patients suffering with joint complaints, suspected to be some form of rheumatoid arthritis, and which had shown negative results when examined according to conventional methods, were examined by the method according to the invention whereupon elevated measurement values indicating the presence of rheumatoid factors were obtained in 16 cases.

What is claimed is:

1. A method of indicating rheumatoid factors belonging to at least one of the immunoglobulin classes IgM, IgG and IgA in an aqueous sample, which method comprises
    (a) pacifying any complement factor C1q present in the sample,
    (b) thereafter reacting the sample with soluble, aggregated immunoglobulin labelled with one or more analytically indicatable atoms or groups to form aggregates between rheumatoid factors and the aggregated, labelled immunoglobulin, said aggregates being precipitated out,
    (c) separating the precipitate, and
    (d) thereafter measuring indicatable atoms or groups in the precipitated phase formed and/or in the solution.

2. A method according to claim 1 wherein the labelled aggregated immunoglobulin belongs to the IgG class.

* * * * *